(12) United States Patent
Withers et al.

(10) Patent No.: US 8,665,423 B2
(45) Date of Patent: Mar. 4, 2014

(54) METHOD AND APPARATUS FOR INVESTIGATING A NON-PLANAR SAMPLE

(75) Inventors: Michael J. Withers, Cambridge (GB); Bryan E. Cole, Cambridge (GB)

(73) Assignee: TeraView Limited, Cambridge (GB)

( * ) Notice: Subject to any disclaimer, the term of this patent is extended or adjusted under 35 U.S.C. 154(b) by 339 days.

(21) Appl. No.: 10/569,374

(22) PCT Filed: Aug. 27, 2004

(86) PCT No.: PCT/GB2004/003685
§ 371 (c)(1),
(2), (4) Date: Feb. 26, 2007

(87) PCT Pub. No.: WO2005/022130
PCT Pub. Date: Mar. 10, 2005

(65) Prior Publication Data
US 2007/0257216 A1   Nov. 8, 2007

(30) Foreign Application Priority Data
Aug. 27, 2003  (GB) .................................. 0320080.5

(51) Int. Cl.
*G01J 3/00*   (2006.01)
(52) U.S. Cl.
USPC .......................................................... 356/51
(58) Field of Classification Search
USPC .................... 356/477, 496, 503, 504, 511, 51
See application file for complete search history.

(56) References Cited

U.S. PATENT DOCUMENTS

| | | | |
|---|---|---|---|
| 3,712,979 A * | 1/1973 | Padgitt | ..................... 362/296.05 |
| 5,067,817 A | 11/1991 | Glenn | |
| 5,444,746 A | 8/1995 | Okamoto et al. | |
| 5,450,203 A | 9/1995 | Penkethman | |
| 2002/0018216 A1 | 2/2002 | Kawasaki et al. | |
| 2004/0065831 A1 * | 4/2004 | Federici et al. | ............ 250/341.1 |
| 2005/0023470 A1 * | 2/2005 | Ferguson et al. | .......... 250/358.1 |
| 2005/0082479 A1 * | 4/2005 | Wallace et al. | ............... 250/330 |

FOREIGN PATENT DOCUMENTS

| | | |
|---|---|---|
| EP | 1 355 127 A2 | 10/2003 |
| GB | 1 206 668 A | 9/1970 |
| GB | 2 190 487 A | 11/1987 |
| GB | 2 360 186 | 9/2001 |

(Continued)

OTHER PUBLICATIONS

Mittleman, Daniel M., et al., "T-Ray Imaging"; IEEE Journal of Selected Topics in Quantum Electronics, vol. 2, No. 2, Sep. 1996, pp. 679-692.

(Continued)

*Primary Examiner* — Tarifur Chowdhury
*Assistant Examiner* — Jonathan Hansen
(74) *Attorney, Agent, or Firm* — Dickstein Shapiro LLP

(57) ABSTRACT

Method and apparatus for investigating a sample particularly a pharmaceutical tablet. An emitter and/or the sample are initially positioned so that the emitter is at a predetermined distance and normal angle to a first point on a surface of the sample. The emitter then irradiates the sample with radiation having a plurality of frequencies in the range from 25 GHz to 100 THz at a plurality of points on the surface of the sample. Relative motion is possible between the emitter and the sample so that the surface of the sample can be tracked to maintain the predetermined distance and normal angle at each of the plurality of points, and allow radiation transmitted and/or reflected from the sample at the plurality of points to be detected. This has particular application to imaging the structure or composition of a coating on a pharmaceutical tablet.

21 Claims, 10 Drawing Sheets

(56) References Cited

FOREIGN PATENT DOCUMENTS

| GB | 2 385 415 | 8/2003 |
| WO | WO-01-51915 A1 | 7/2001 |
| WO | WO 02/057750 | 7/2002 |
| WO | WO 03042670 A1 * | 5/2003 |

OTHER PUBLICATIONS

Mittleman, Daniel M., et al., "T-ray tomography", Optics Letters, vol. 22, No. 12, Jun. 15, 1997, pp. 904-906.

Ferguson, Bradley, "T-ray computed tomography", Optics Letters, vol. 27, No. 15, Aug. 1, 2005, pp. 1312-1314.

* cited by examiner

METHOD AND APPARATUS FOR INVESTIGATING A NON-PLANAR SAMPLE

The present invention relates generally to the field of apparatus and methods for investigating a three dimensional non-planar sample and most particularly to imaging the surface layer or layers of a non-planar sample. More specifically, the present invention relates to investigating the surface layer or layers of a tablet for the purpose of analysing the coating of the tablet.

In the field of pharmaceutical tablet manufacture, it is often necessary to apply a coating to a tablet. Tablet coatings serve a number of purposes, such as the enhancement of the tablet's shelf-life, palatability, solubility and visual appeal, in that a coating can provide a coloured exterior. Often tablets have coatings comprising more than one layer.

A method of non-destructive characterisation of a tablet's coating is desirable for monitoring quality control in the manufacture of tablets and other three dimensional coated compositions.

NIR spectroscopy has been used to image pharmaceuticals, as described in the article entitled "A near infrared view of pharmaceutical formulation analysis" by Lewis, Carroll and Clarke published in NIR News Vol. 12, No. 3 (2001). The technique however, is affected by scattering issues, and therefore is not able to probe much below the surface of the sample.

Another approach uses Raman spectroscopy. This technique obtains Raman image data and applies multi-variant image processing thereto. This technique, once again, can only acquire an image of the surface of the tablet. A further problem, however, is that the surface of the tablet sample needs to be very flat. This flatness requirement is imposed by the limited depth-of-field of Raman imaging, due to the need to use very high numerical aperture objectives in order to collect the signal available.

Another problem with Raman spectroscopy is that it cannot be used on chemicals that fluoresce, as this masks the Raman signal. Further, high power illumination is a feature of Raman spectroscopy, and this can lead to heating and changes in chemistry of the sample being imaged.

According to one aspect, the present invention provides a method of investigating a non-planar sample comprising:
  providing at least one emitter for irradiating the non-planar sample;
  irradiating the sample with radiation having at least one frequency in the range from 25 GHz to 100 THz at a plurality of points on a non-planar surface of the sample, while maintaining a predetermined position of the or an emitter with respect to a point on the sample for each of the plurality of points;
  detecting radiation transmitted and/or reflected from the sample at the plurality of points.

This aspect of the invention enables non-planar objects, such as pharmaceutical tablets to be accurately investigated, and imaged if required. In particular, it enables one or more surface layers or coatings of tablets to be investigated, such as to ensure the integrity of the one or more coatings.

By maintaining the one or more emitters at a predetermined position on the sample for each of the points, tracking of the sample surface in more than two dimensions can be effected, enabling a non-planar sample to be investigated. Therefore this feature, combined with the use of THz radiation enables one or more surface layers to be analysed.

The detected radiation may be analysed to determine characteristics of one or more surface layers of the sample or a geometry of one or more surface layers of the sample. The characteristics determined may relate to the thickness of one or more surface layers of the sample.

Preferably this aspect of the invention further comprises generating an image of one or more surface layers of the sample using the detected radiation. It is also preferable that the predetermined distance corresponds to a focal distance of the emitter.

It is also preferable that the predetermined position comprises:
  a) a predetermined distance between a point on the sample and an emitter; and
  b) an irradiation axis of the emitter at a predetermined angle of incidence to the point on the sample.

In this regard, the irradiation axis may be the primary direction of radiation incident on the sample surface. The irradiation axis may be arranged at a normal incidence to the point on the sample. Where the emitter is housed in a probe head, the irradiation axis may correspond to the longitudinal axis of the probe head. Alternatively, if the emitter is provided in a probe head, the longitudinal probe axis may intersect the point at normal incidence, but the irradiation axis may not be strictly parallel to the probe axis. Instead, the system may be a so-called "near normal incidence" system, in which the emitted and reflected beams are spatially separated.

It is preferable that the emitter and/or the sample are actuated to enable the emitter to move relative to the sample about a first trajectory from the first point such that the plurality of points lie on the first trajectory. Further, the emitter may be repositioned at an angle to the first position, the angle lying on a second trajectory, such that the second trajectory is in a plane perpendicular to a plane of the first trajectory; the actuating and irradiating steps are repeated about a third trajectory parallel with the first trajectory; and radiation transmitted and/or reflected from the sample is detected at a second plurality of points about the third trajectory. The repositioning of the emitter may then be repeated along a range of angles along the second trajectory in order to obtain additional detection measurements.

According to another aspect the present invention provides apparatus for investigating a sample having a non-planar surface, the apparatus comprising:
  at least one emitter for irradiating the sample with radiation having at least one frequency in the range from 25 GHz to 100 THz at a plurality of points on a surface of the sample; and
  a detector for detecting radiation transmitted and/or reflected from the sample at the plurality of points on the sample,
  wherein the or an emitter is maintained at a predetermined position with respect to a point on a non-planar surface of the sample and the predetermined position is maintained with respect to each of the plurality of points.

Preferably the apparatus further comprises means for actuating the emitter and/or the sample to enable the emitter to move relative to the sample about a first trajectory from the first point such that the plurality of points lie on the first trajectory. This means for actuating may comprise a robot arm. Preferably the robot arm is at least a five-axis motion system, which may have three axes of translational motion and two axes of rotational motion.

It is also preferable that each of the at least one emitters are housed in a fiber-coupled probe head. A probe of the type described in GB 2371618 may be used. These probe heads may be fixed or attached to a robot arm. Where the probe heads are fixed, means will be provided to move the sample relative to the probe head or heads, such as using a conveyor belt in a production environment.

According to further aspect, the present invention provides a method of investigating a non-planar sample comprising:

positioning a scanning means a predetermined distance from a first position on the sample surface;

actuating the scanning means and/or the sample to enable the scanning means to move relative to the sample about a first trajectory from the first position;

irradiating the sample about the first trajectory with radiation having a plurality of frequencies in the range from 25 GHz to 100 THz;

obtaining reflection and/or transmission measurements at a plurality of positions about the trajectory.

Alternatively, a plurality of emitters may be provided each at a predetermined position respective to different points on the non-planar surface.

These aspects of the present invention utilise radiation in the infra-red (IR) and Terahertz frequency range from 25 GHz to 100 THz. It is to be appreciated that in this type of tomography technology, all such radiation is colloquially referred to as THz radiation, particularly that in the range from 25 GHz to 100 THz, more particularly that in the range of 50 GHz to 84 THz, and especially that in the range from 100 GHz to 50 THz.

The present invention will now be described with reference to the accompanying Figures, in which:

FIG. 1 illustrates a schematic diagram of a THz imaging system according to an embodiment of the invention;

FIG. 2 provides a schematic representation of a THz scanning probe scanning around a non-uniform object according to an embodiment of the invention;

Figure 8:
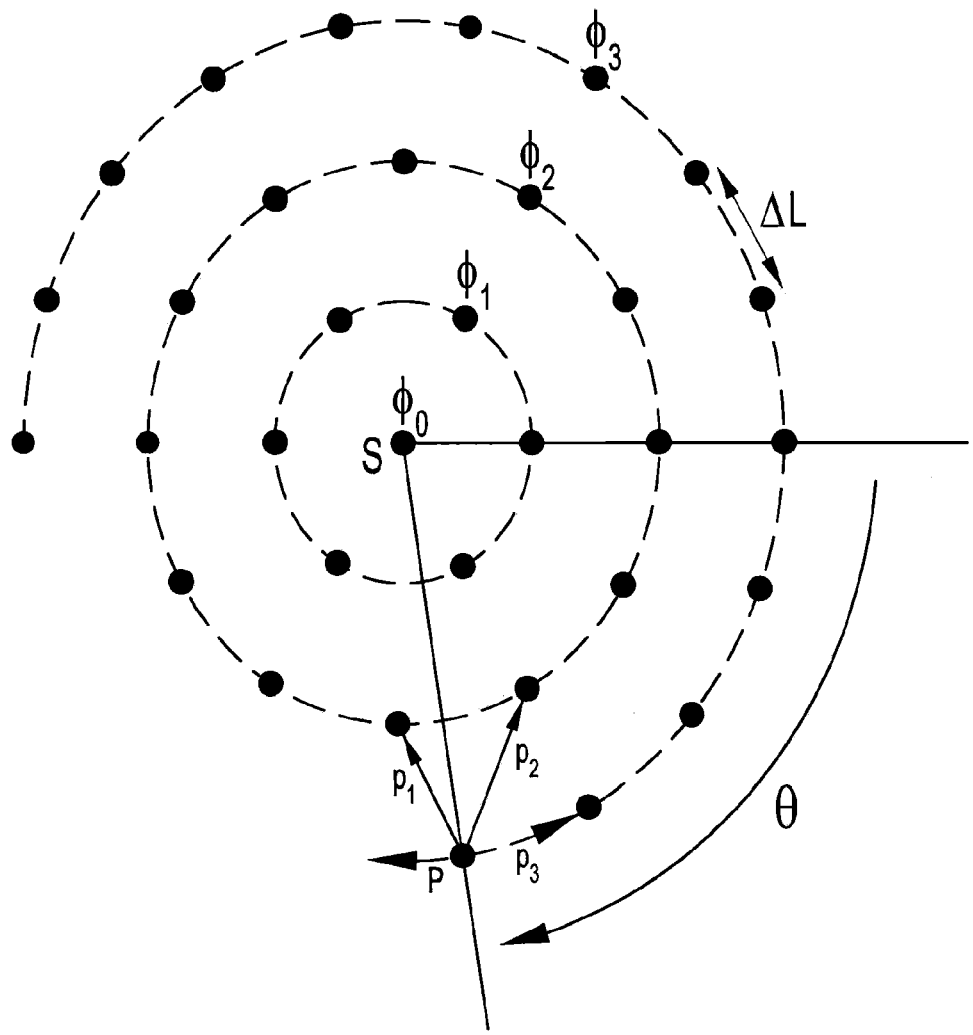

FIG. 8 schematically illustrates the measurement procedure for three θ scans for different values of Φ about a start position and the vectors used in the calculation of the normal vector.

Figure 9:
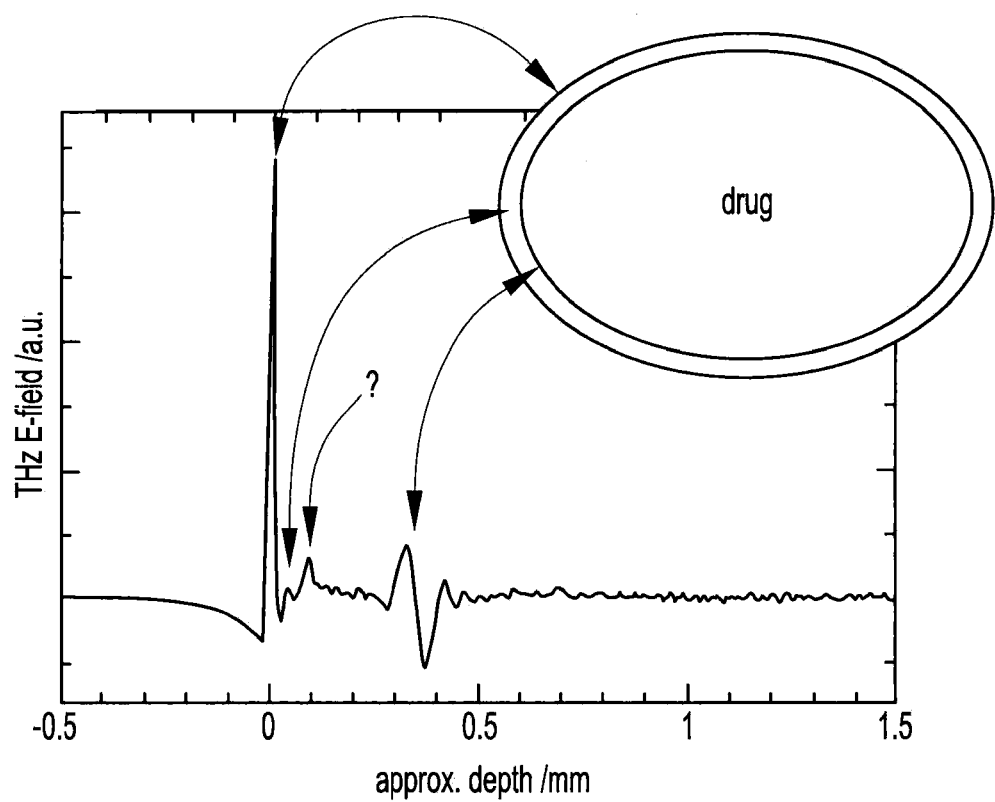

FIG. 9 illustrates a THz waveform obtained using the present invention, and indicates the correspondence of the features in the waveform against a tablet cross-section.

Figure 10:
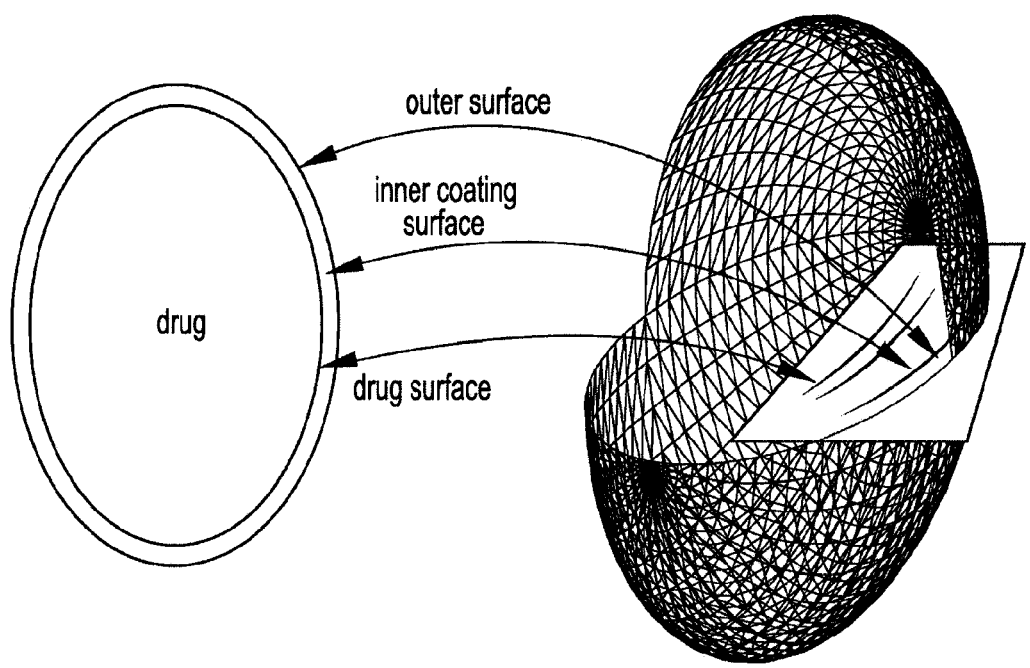

FIG. 10 illustrates a slice through a volume dataset, on the right, and compared with the outline of a tablet, so as to show the different material interfaces.

Figure 11:
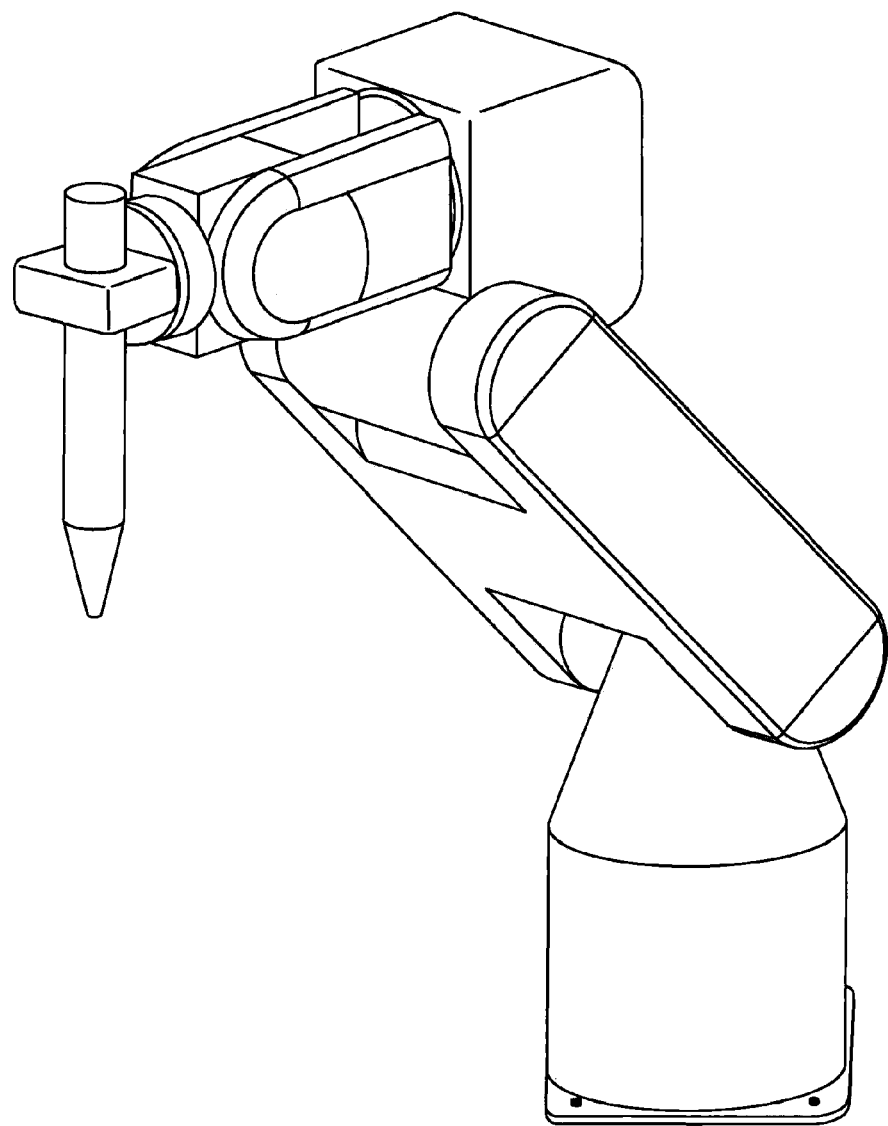

FIG. 11 illustrates a robot arm suitable for automated manipulation of a THz probe head around a target object in accordance with an embodiment of the invention.

Figure 12:
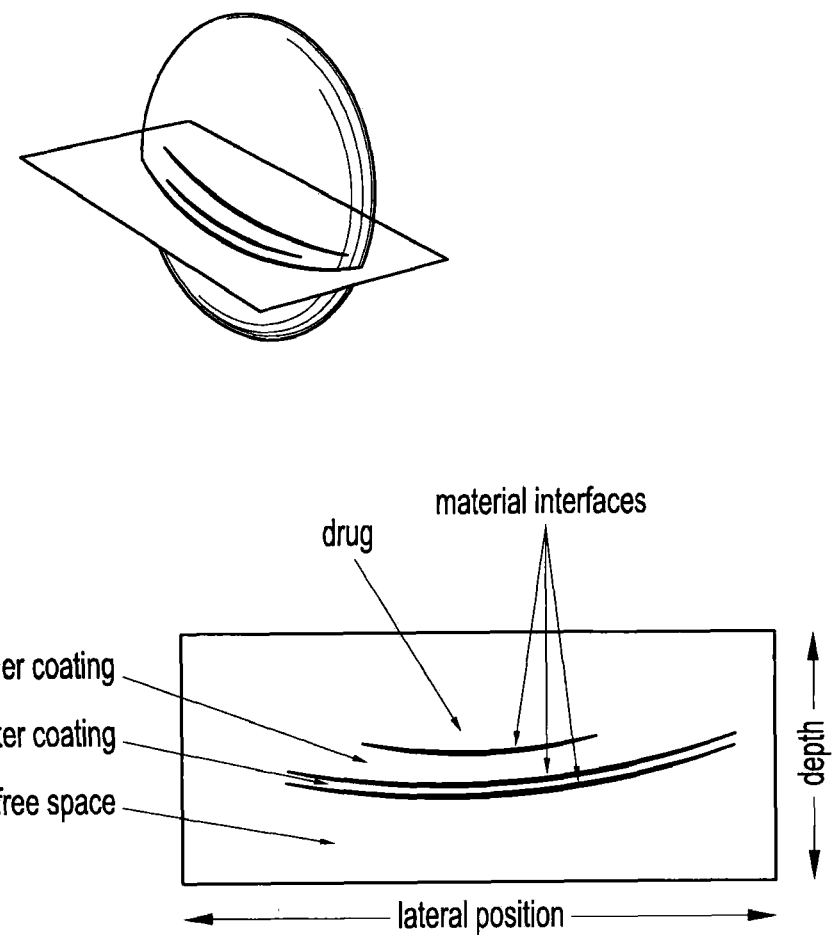

FIG. 12 illustrates a three dimensional data set for the coating structure of a tablet imaged according to an embodiment of the present invention. The Figure also illustrates a slice through the volume dataset plotted to illustrate the coating in cross-section.

Figure 13:
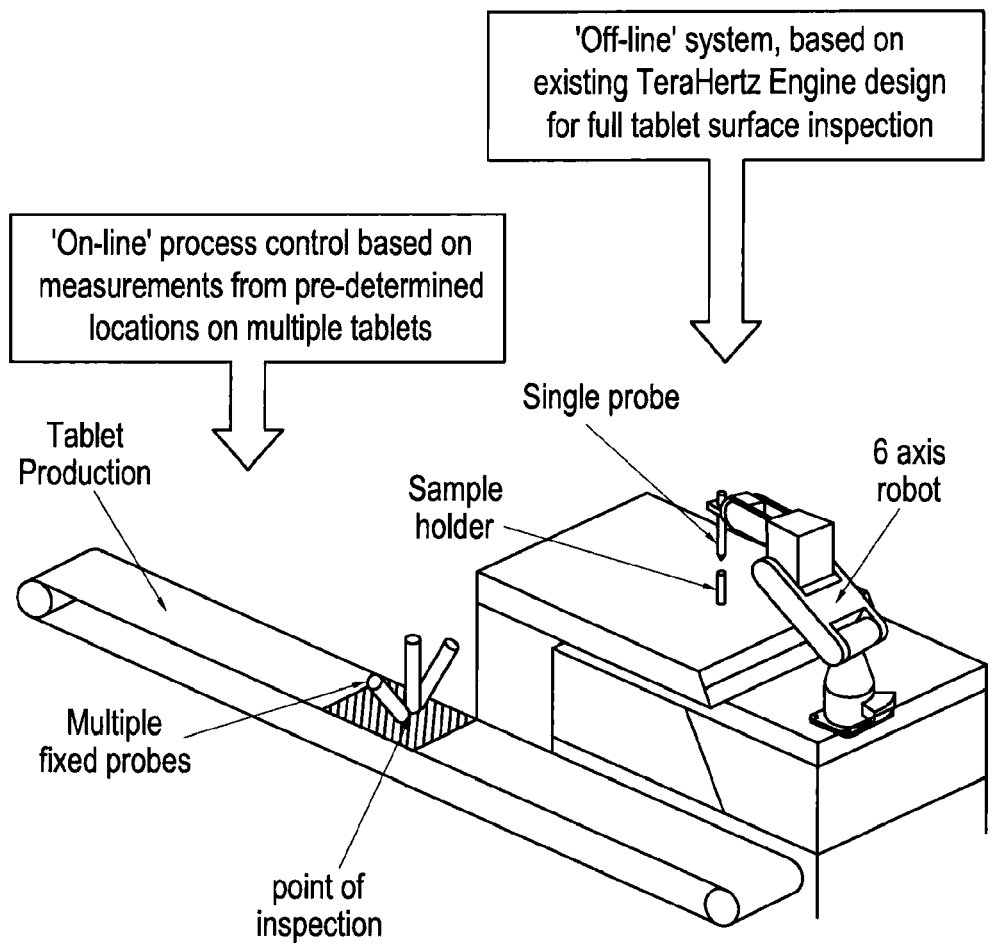

FIG. 13 illustrates examples of a fiber-delivered THz probe, using a robot arm manipulator as used on a production line (on the left) and also in an offline testing system (on the right).

Terahertz pulse imaging has been shown to be a useful imaging modality for non-destructive analysis of internal composition of an object and for other general planar imaging and for spectroscopic analysis of molecular composition. However, the use of THz imaging for the purpose of imaging non-planar objects has been problematic, particularly since the requirements for high spatial resolution and depth-of-focus are conflicting.

More specifically, in a typical THz imaging system, a low THz optical F-number (equivalent to a large numerical aperture) is usually chosen so as to maximise the spatial resolution of the THz imaging in the plane perpendicular to the THz incidence direction. However, the low F-number of the system results in a very limited plane-focus for the system. Thus, non-planar objects are difficult to image, since their surface outline extends over a larger range than the THz depth-of-field can accommodate.

Furthermore, highly curved or non-planar surfaces tend to reflect the incident THz away from the THZ detection system resulting in a small or negligible THz signal.

Figure 1:
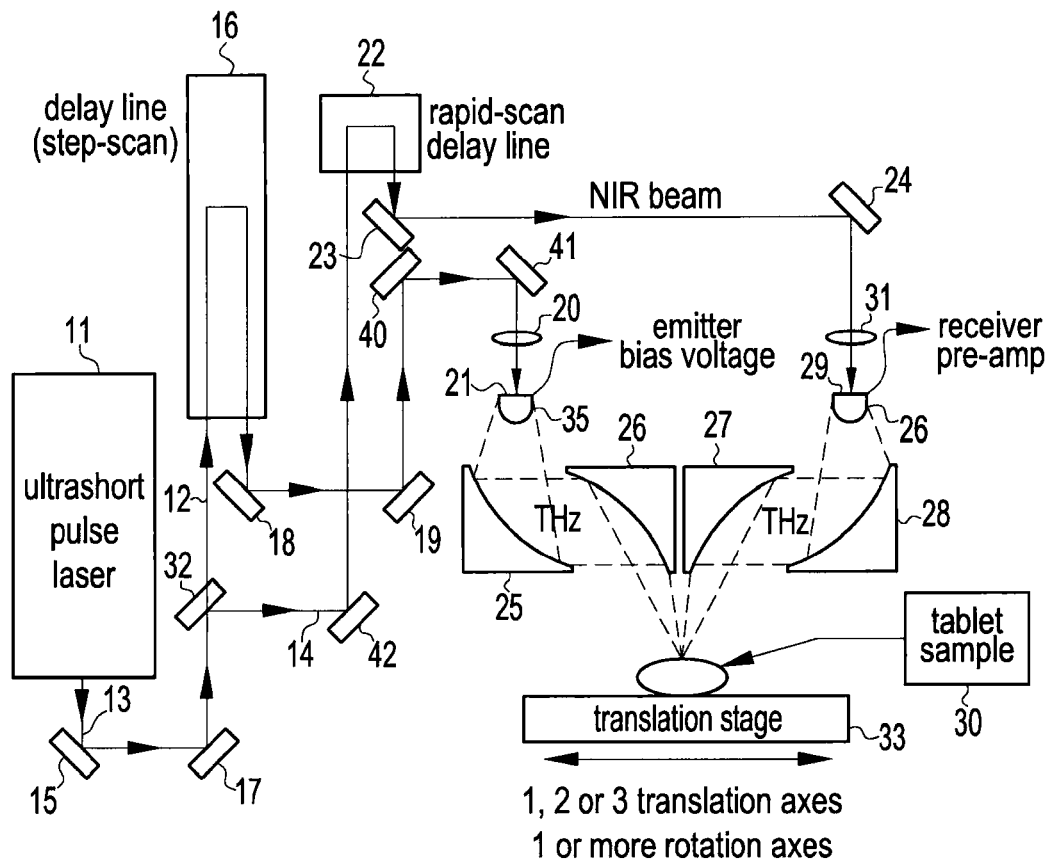

The embodiments of the present invention have been able to address these problems and an apparatus according to one embodiment of the present invention, as shown in FIG. 1, can be used to THz scan a non-planar object, such as a rounded pharmaceutical tablet.

The apparatus of FIG. 1 comprises an ultra-short pulse laser 11 which may be, for example, Ti:sapphire, Yb:Er doped fibre, Cr:LiSAF, Yb:silica, Nd:YLF, Nd:Glass, Nd:YAG or Alexandrite laser. This laser 11 emits pulses of radiation 13, such as a collimated beam of pulses, each of which comprise a plurality of frequencies. This pulse is reflected by first mirror 15 and second mirror 17 into beam splitter 32. The beam splitter splits the beam into a pump pulse 12 that is used to irradiate the sample and a probe pulse. 14 that is used during detection.

The pump pulse 12 is directed into first scanning delay line 16. Scanning delay line 16 is a static delay, or a step-scan, which adjusts the relative path-lengths between the pump and probe beams. The output pump pulse from the first scanning delay line is then directed by mirrors 18, 19, 40 and 41 into lens 20, which is preferably an aspherical lens, when used for NIR. Lens 20 focuses the pump pulse onto a source 21, which preferably comprises a frequency conversion member and a bow-tie emitter. The frequency conversion member is configured to mix the incident radiation in order to output radiation derived from the differences of the input frequencies, so-called difference frequency generation. This technique is described in more detail in GB 2 347 835.

The emitter 21 abuts a hyper-hemispherical lens 35. The terahertz beam that is output from the emitter 21 is directed by the first silicon hyper-hemispherical lens 35 towards a first parabolic mirror 25. The beam is then reflected off the first parabolic mirror 25 and onto second parabolic mirror 26, which directs the radiation onto sample 30. The sample may be replaced with a reference sample in order to remove instrumental artefacts from the final results. The radiation which is reflected from sample 30 is then collected by third parabolic mirror 27 and onto a fourth parabolic mirror 28 which directs the reflected radiation onto a second hyper-hemispherical lens 36 and onto a detector 29, such as a photoconductive detector. The terahertz beam as reflected off the sample is re-combined with the probe pulse 14 at the receiver 29.

Prior to recombining with the terahertz beam, the probe beam 14 is directed into second scanning delay line 22 by mirror 42. This delay line is a rapid-scanning type and in its simplest form comprises two mirrors that serve to reflect the beam through a 180° angle. These mirrors are then quickly swept backwards and forwards in order to vary the path length of the probe pulse 14. Alternatively the second delay line could be a static delay line and the first delay line a scanning delay line, as the location of each type of delay line does not matter, provided the relative path lengths of the pump and probe beams can be matched.

The probe beam 14 output from the second scanning delay line 22 is then reflected off first probe beam mirror 23 onto second probe beam mirror 24 which directs the probe beam through lens 31, which is an aspherical lens when used to focus NIR beams. This lens 31 focuses the probe beam onto the receiver 29 for combining with the reflected terahertz beam.

The sample introduces a time delay in the path of the terahertz pulse. The delay is dependent on both the absorption coefficient, the refractive index and the position of the sample. In order to obtain a detection signal, the frequency component of the probe beam must be in phase with a frequency component of the pump beam. Variation of the first and second scanning delay line allows the phase of the probe beam and/or pump beam to be swept with respect to the pump beam and/or probe beam and thus allows for measurement of the delay time of each frequency component which passes through the sample.

While the apparatus has been described in relation to pulses, such as a collimated beam of pulses, it is to be appreciated that the present invention may also be implemented using a continuous wave (CW) source. Continuous wave generation is described in detail in European patent application number 01907935.9.

The THz emitter 21, the THz receiver 29, the hyper-hemispherical lenses 35, 36 and the parabolic mirrors 25, 26, 27, 28 may be provided in a probe head which is fed by an optical fibre. In this configuration, optical fibres would deliver the pump and probe pulses 12, 14 to the probe head. At the output of the optical fibres, lenses 20 and 31 in the probe head would receive the pump and probe pulses respectively and focus the pulses onto the emitter 21 and receiver 29 respectively.

In the FIG. 1 apparatus, the sample is placed on a translation stage 33. In this embodiment of the invention the stage has three axes of translational motion and two axes of rotational motion. In this way, the position of the object can be manipulated so that during the scanning processing the probe head is maintained at normal incidence to the surface of the object and at a predetermined distance. This predetermined distance should be equivalent to the focal length of the THz beam. Hence, the surface of the object is tracked and distortions due to refraction at the tablet surface are avoided, thereby allowing greater accuracy when investigating the outer layer or layers of the object.

When the sample lies on the stage 33, some areas of the sample will not be accessible to the probe head, due to the requirement for support points. Hence, with this arrangement, it is not possible to scan the entire object in a single scan. To scan the entire object, the object needs to be repositioned after the first scan, so as to expose the inaccessible regions, and then scan those regions to complete the dataset. If, however, a single scan of nearly the entire object is required, one approach is to use vacuum tweezers or other such grasping mechanism. This will enable the regions that are inaccessible to the THz scanning head to be revealed. A small inaccessible region remains, even when using a grasping mechanism such as vacuum-tweezers.

Therefore, with this approach of using a 5-axis motion system, the THz focal spot is maintained at a fixed position and the motion system is used to translate and rotate the object with respect to the focus. To undertake the scanning, a user can approximate boundaries to the region of interest in terms of upper and lower limits on the x, y and/or z coordinate axes as well as its rotational axes. Alternatively default limits may be utilised, such as ones that are based on the maximum range of movement by the probe head.

Figure 2:
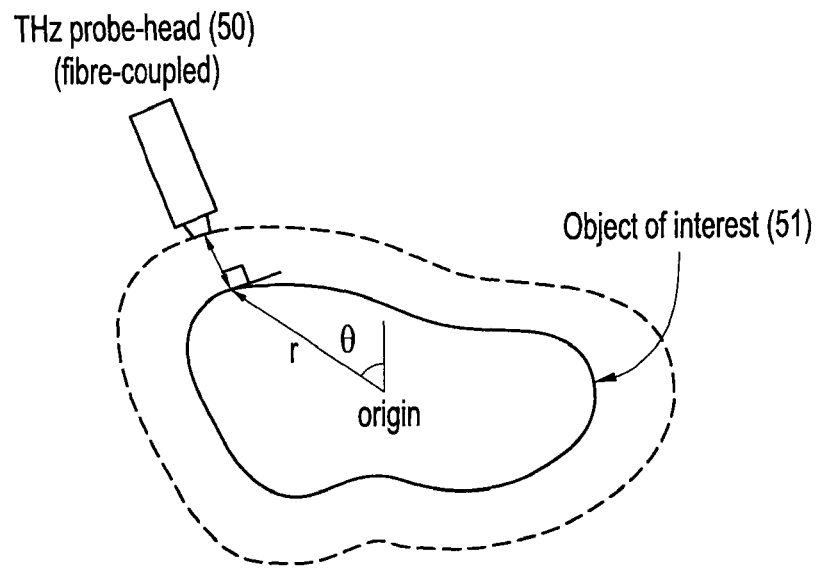

According to an alternative embodiment, the scanning head is given motion capabilities in addition to, or instead of, the stage 33. With reference to FIG. 2, a THz probe head 50 is illustrated adjacent an object 51 to be scanned which has an irregularly shaped or non-planar surface. The THz beam is delivered to the probe head 50 by an optical fiber. The trajectory of the probe head 50 about the object is indicated by the dashed line. This trajectory maintains the probe head at a constant distance from the surface of the object and with the orientation perpendicular to the object surface.

Fiber-coupled THz devices allows the THz source and/or detector to be freely positioned while leaving the NIR-optical components of the system fixed. In this regard, the THz devices used to convert the NIR optical pulses to/from THz pulses are compact, typically a few centimeters in dimension, and therefore readily able to be incorporated into a reasonably sized and positionable probe head.

Therefore, in this embodiment of the invention, the probe head is freely positionable about the object of interest. It has three axes of translational motion and two axes of rotational motion. Therefore, if the surface geometry of the object is known, the probe head can be moved across the object while maintaining a perpendicular orientation and constant distance to the object surface. This arrangement can therefore overcome the problem of object surface curvature.

To achieve this ability to freely position the probe head, a robot arm may be utilised, as illustrated in FIG. 11. Such a robot arm would be suitable for automated manipulation of a THz point probe around an object to be scanned.

A still further alternative is for both the probe head 19 and the stage 33 to be capable of motion. For instance, the probe head could be translatable and the stage rotatable. The key point is that there is relative motion between the stage and the probe head to maintain the probe head at normal incidence to the surface of the object and at a predetermined distance.

To maintain the probe head at normal incidence and predetermined distance from the object, the system needs to have knowledge of the surface geometry of the object. This may be predetermined and stored in a memory associated with the scanning system. This is beneficial when the invention is used to image the same type of object, such as sample tablets from a production line.

Therefore, another embodiment of the present invention relates to a technique for scanning an object in order to determine its surface geometry. This technique can be used to image the surface layers of the object, particularly closed surface objects.

A closed surface is one that wraps around on itself, such as a sphere or ellipsoid. Objects with a closed surface geometry include pharmaceutical tablets or pills. Closed surfaces are best described in polar coordinates, being $r=F(\theta,\Phi)$, where r is a vector from a position inside the object to a position R on the surface, and $\theta,\Phi$ are the angular coordinates of the position.

Figure 3:
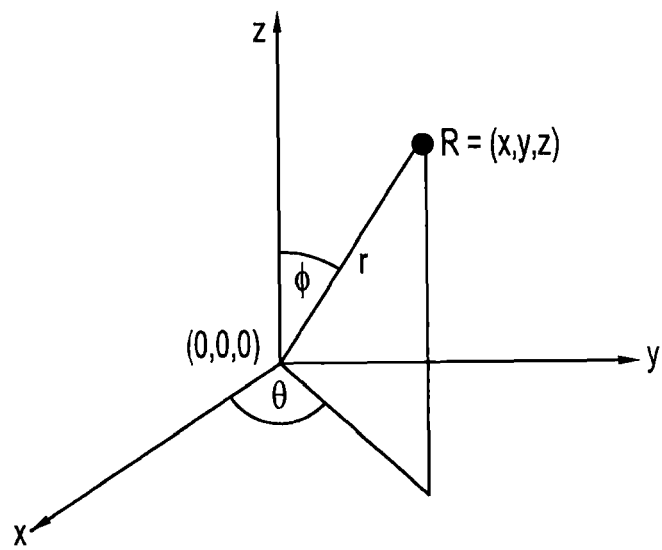
FIG. 3 illustrates polar coordinates on a standard x,y,z coordinate axes.

In this regard, with reference to FIG. 3, Cartesian coordinate axes (x,y,z) are illustrated overlying a position R, with the origin being at (0,0,0), $\Phi$ is the angle between the vector r (from the origin to position R) and one of the Cartesian coordinate axes, in this case, the z axis. The angular coordinate $\theta$ is the azimuthal angle relative to the vector r, on the x,y plane. Similarly, in FIG. 2, polar coordinates applicable to the two dimensional representation are illustrated. The vector r extends from the origin (i.e. (0, 0, 0) to a position on the surface of the object, and θ is the angle between the vector r and one of the Cartesian coordinate axes.

Where a closed surface geometry is being determined, the limits of the surface will be specified in terms of the limits on the angular coordinates θ and Φ.

An approximate position for the coordinate-origin needs to be specified, which should lie inside the sample-volume. The operator can specify this. The exact location of this origin is not critical but a position close to the centre of the volume is desirable.

A spatial resolution value, ΔL should also be specified, which corresponds to the approximate spatial resolution required (e.g. 50 μm). With reference to FIG. 8, the spatial resolution is visually indicated, in that it is the approximate distance between consecutive points in a θ scan.

Figure 4:
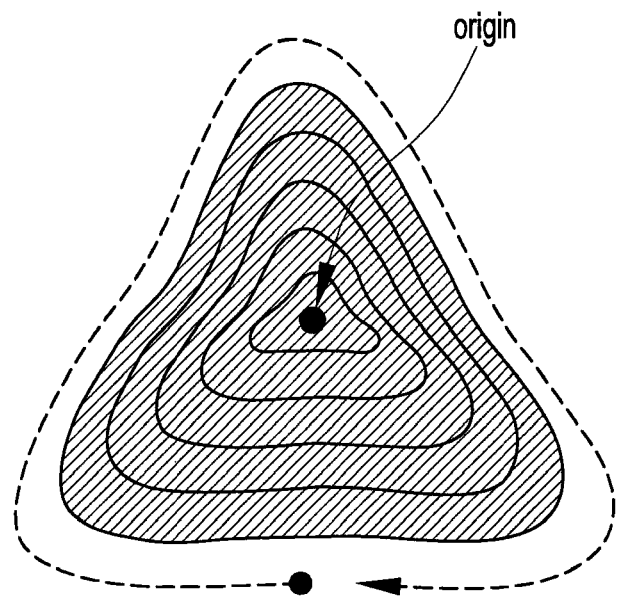
FIG. 4 illustrates a surface geometry and generally how it is expanded upon, when using a scanning technique according to an embodiment of the present invention.

To scan the entire closed surface, θ must be measured from 0 to 2 π and Φ from 0 to π. This is achieved based upon the continuous expansion of a "known area" beginning at a point of initialisation on the surface or "start-point". The start-point for the scan represents the point on the sample surface at which scanning begins. There is also a "start orientation" which represents the direction normal to the sample surface at the Start Point. This iterative process is illustrated generally in FIG. 4. That is, FIG. 4 shows a projection of part of a closed surface. The THz scan is performed about the start point, as shown by the dotted trajectory around the perimeter of the object. The result of this first scan is indicated by the first dark outline out from the start point. This area provides a first indication of the object surface, which is in effect the "known surface" after the first iteration. The area of the "known surface" can be expanded upon by repeated scans about the perimeter of the object for increasing values of Φ until the entire closed surface is known.

Before undertaking this iterative scanning procedure, the probe head is first initialised, which involves it being positioned so as to focus on a point on the sample surface, and optimised to normal incidence such that the THz signal and bandwidth are maximised. This effectively sets out the Φ=0 position. This may be performed manually or be automated.

Figure 5:
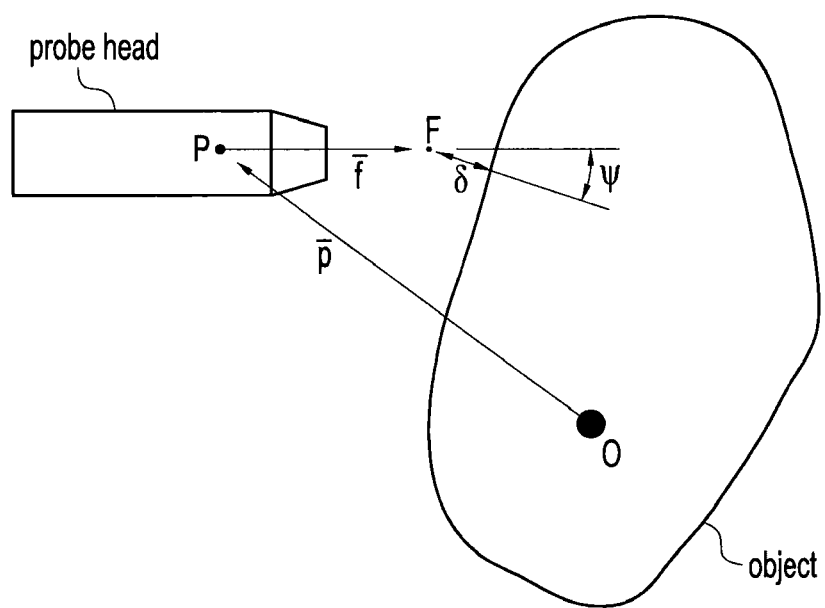
FIG. 5 illustrates the vectors involved with aligning a probe to an initial scan position.

FIG. 5 illustrates the general procedure for aligning the probe to the initial scan position. The position of the probe head 50 is described in terms of a vector $\underline{p}$ from the predetermined, and possibly arbitrarily chosen, origin O to a datum P on the probe head.

The position vector $\underline{p}$ is determined from the state of the mechanical scanning system (not shown). Such scanning systems comprise a number of translation and/or rotation units. Each unit maintains information on its current position. The overall vector $\underline{p}$ is therefore determined from the sum of the position vectors obtained from each component of the scanning system.

The focal point F of the THz beam and the THz collection optics is at a known position with respect to the scanning probe head. The vector between the datum P on the probe head and the focal point F is labelled $\underline{f}$ in FIG. 5. Thus, the overall position of the THz focal point is the sum of vectors $\underline{p}$ and $\underline{f}$. It follows that the position of the THz focus F with respect to the origin O is known at all times.

In order to align the probe head at its Start Position prior to performing an initial scan over the object surface, the THz focus, F is brought to a position co-incident with a point on the object surface. Also, the orientation of the probe head should be adjusted to correspond to the direction normal to the object surface at point F. A displacement and angular misalignment between F and the object surface are to be expected, so initially these conditions are unlikely to be met.

The displacement of F from the object surface is labelled δ in FIG. 5, while the angular misalignment is represented by an angle ψ. Minimisation of δ and ψ may be achieved manually by the user or via an automated process.

Manual minimisation involves comparing a real-time display of the THz waveform obtained while scanning the rapid-scanning delay-line at a frequency over 0.1 Hz and a reference waveform. The reference waveform is obtained by placing a mirror or other highly reflective planar object at the focal position F, such that the THz probe head axis along vector $\underline{f}$ is normal to the mirror surface.

Figure 6:
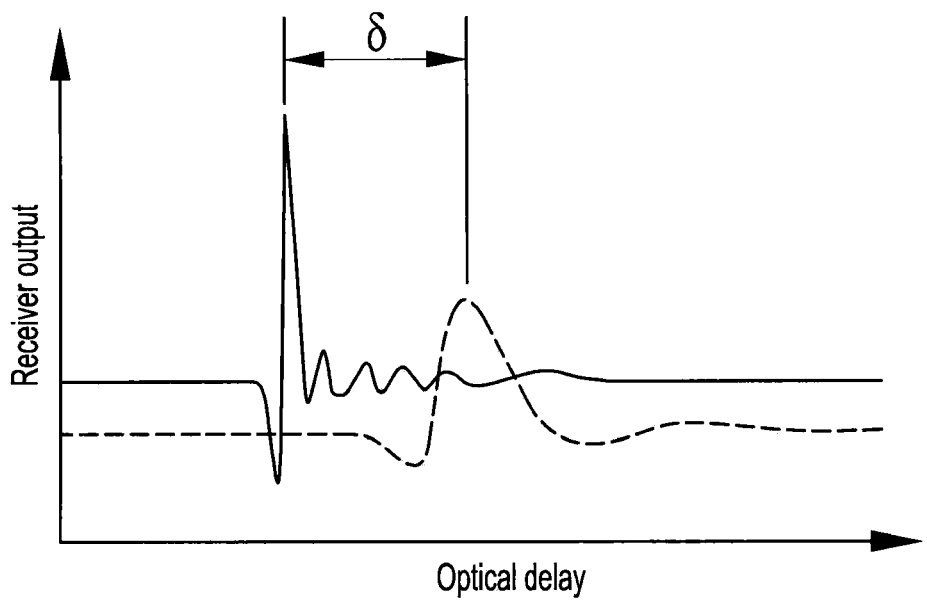
FIG. 6 illustrates a schematic of an initialising THz waveform compared against a reference waveform when the emitter is sub-optimally aligned.

With reference to FIG. 6, the form of the THz waveform is illustrated, being the lower dotted trace, together with the reference waveform, being the upper solid-line trace. The traces have been offset for clarity. The y-axis is the receiver output and the x-axis units may be considered as either displacement or time-delay.

The displacement δ between the THz focal position and the object surface is also indicated in FIG. 6, being the distance between the maximum peaks of the two waveforms. The observed THz waveform is lower in amplitude and bandwidth (i.e. broader) than the reference pulse, which is indicative of the probe head being sub-optimally aligned.

Figure 7:
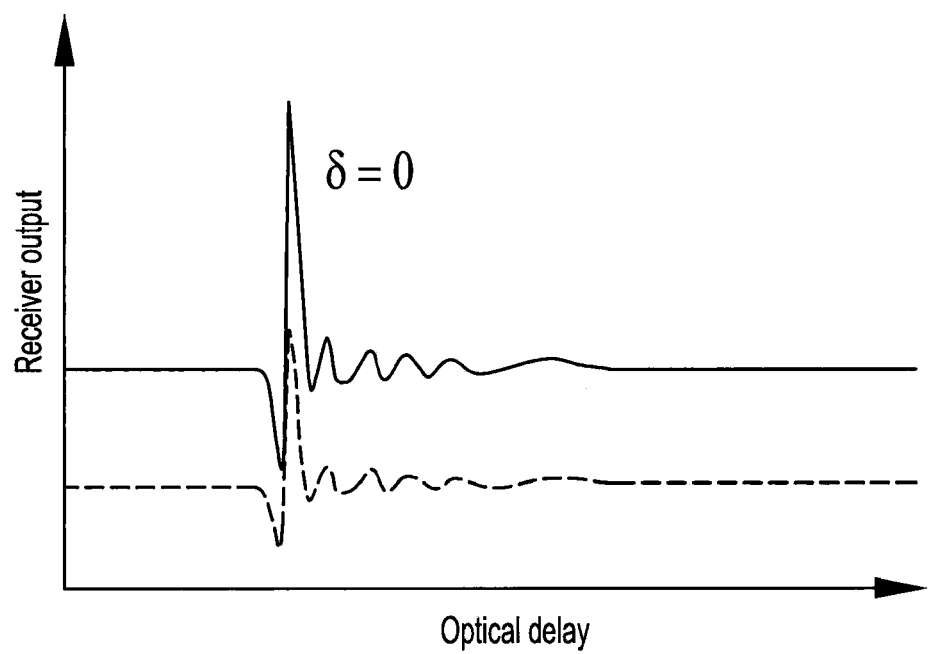
FIG. 7 illustrates a schematic of an initialising THz waveform compared against a reference waveform when the emitter is optimally aligned.

At the optimum alignment position the THz waveform obtained from the object surface will have a peak (or other feature) at the same optical-delay value as the reference waveform. An illustration of the observed THz pulse obtained from an optimally aligned (i.e. δ=0) probe head is shown in FIG. 7. The observed pulse has a bandwidth similar to that of the reference (i.e. the pulses are similarly 'sharp') and the peaks are co-incident. Also, the amplitude of the observed pulse has been reduced in view of the possibly reduced reflectivity of the object surface.

The optimum orientation of the probe head is obtained by adjustment of the head orientation to maximise the amplitude and the THz bandwidth of the surface-reflected waveform. The limited depth-of-field of the THz optics results in a reduction in the THz bandwidth observed at finite δ, which manifests itself as a broadening of the observed THz pulse. The amplitude of the THz waveform may be less than that of the reference, if the surface reflectivity of the object is less than the mirror used in acquiring the reference, which is not uncommon.

The reflectivity of the object surface may be frequency dependant which may result in some broadening of the observed pulse in comparison to the reference (not shown), however the position of maximum bandwidth will still coincide with the δ=0 position.

Optimal alignment and positioning of the probe head may alternatively be automated. In an automated procedure, the aim is to simultaneously minimise δ and $\Gamma_{BW}$ and maximise A, where $\Gamma_{BW}$ represents the pulse-width of the observed waveform (and is the inverse of the THz pulse bandwidth) and A represents the amplitude of the THz waveform, and where all three are functions of position and orientation.

That is δ(x, y, z, θ, Φ), A(x, y, z, θ, Φ) and $\Gamma_{BW}$(x, y, z, θ, Φ) where x, y and z are the position coordinates of the probe head and θ, Φ represent the angular coordinates specifying the orientation of the probe head. The minimum value of $\Gamma_{BW}$ will correspond to the condition Ψ=0. The minimum/maximum values of these functions may be found using well known iterative searching algorithms. For example, see *"Numerical Recipes in C:The Art of Scientific Computing", $2^{nd}$ Edition*, by W. H. Press, S. A. Teukolsky, W. T. Vetterling and B. P. Flannery. pub. Cambridge University Press, 1992 ISBN 0 521 43108 5.

Once aligned, the probe head is then used to direct THz radiation at the sample, and a THz waveform recorded. Based on the origin position and the known focal position on the surface at Φ=0, the distance $r_0$ from the origin to that surface position can be computed using this waveform. Referring to FIG. 4, this part of the process essentially determines all the parameters relating to the start point.

With the first surface position known, other surface positions can be determined. In this regard, maintaining the focal distance $r_0$ fixed, the probe is moved so that the current value of Φ is incremented by $\Delta\Phi_0$ to obtain a new phi value, $\Phi_1$:

$$\Phi_1 = \Phi_0 + \Delta\Phi_0\Phi_0 + (\Delta L/r_0) \quad (1)$$

Hence the value of increment is dependent upon the required spatial resolution. So where a high quality spatial resolution is required, $\Delta\Phi_0$ will only be small. The above formula is only a guide in choosing a value for $\Delta\Phi_i$. For cases where large deviations between the surface normal direction and the position vector r are expected, smaller values of $\Delta\Phi_i$ may be chosen to improve accuracy.

At this new position, with the phi value of $\Phi_1$ and r kept fixed, the probe is activated to perform a non-linear line scan over a trajectory about the new phi value. Referring again to FIG. 4, the dotted line represents the trajectory path of the scan head, and the first black ring surrounding the start point represents the positions on the object's surface that the scan head would irradiate for the new phi value. Therefore, the new surface position for $\Phi_1$ will be somewhere on this ring.

The trajectory is determined by incrementing θ over the range 0 to 2π in n steps, where n is given by:

$$n = 2\pi r \sin(\Phi)/\Delta L \quad (2)$$

and n is rounded up to the nearest integer. Therefore, n is also dependent upon the required spatial resolution, so that there will be a greater number of measurements where a high quality spatial resolution is required. The number of steps n will change for each Φ-value. This equation is a simple guide in choosing the number of θ-steps required. A larger number of steps may be chosen to improve accuracy.

If n is found by this method to be less than 6, it should be rounded up to 6 in the interests of maintaining a reasonable degree of resolution (e.g. for small Φ). It is to be appreciated that the number 6 has been arbitrarily chosen to provide a convenient number of points around the start point for calculation of surface normals.

This line-scanning process involves acquiring a series of THz waveforms over the θ trajectory. That is a THz waveform will be determined for each of the n raster-positions about the trajectory. During the line scan, the distance between the probe head and the origin remains fixed at the position determined for the $\Phi_0$ point.

At the completion of the line scan, the results can be used to calculate the actual surface position over the scan, so replacing the estimated values. The estimated values for the surface position and orientation can be those determined for the $\Phi_0$ point or be calculated based on interpolation from the closest points found in the previous line-scan dataset.

Hence, using the THz waveforms obtained about the surface positions at $\Phi_1$ and the information known about the previous surface position at $\Phi_0$, it is possible to determine $r_1$ for each of the n positions, where each $r_1$ is the actual distance between the surface point and the "origin" position.

After each individual point measurement has been performed, the actual surface position may be calculated from 1) the estimated position and 2) the observed distance between the THz focus F and the object surface. It is the set of "known" points that are used to calculate the surface normal vectors.

Surface normals (i.e. vectors normal to the surface) for each of the surface positions need to be calculated from the measurement points in the previous line-scan.

The calculation of the surface normal vector for the most recently acquired point is made using the vectors defined by the distance between the current point and the surrounding points. This is illustrated in FIG. 8. The last acquired point is labelled P in this figure. Three vectors describing the transformation from P to its nearest neighbouring known points (i.e. actual positions) are shown as $\underline{p_1}, \underline{p_2}, \underline{p_3}$. Any two of these vectors can be used to calculate a normal vector, as the cross product (also known as the vector product) of the two vectors. That is:

$$\underline{n_1} = \underline{p_1} \wedge \underline{p_2}/|p_1||p_2|$$

$$\underline{n_2} = \underline{p_2} \wedge \underline{p_3}/|p_2||p_3|$$

$$\underline{n_3} = \underline{p_1} \wedge \underline{p_3}/|p_1||p_3|$$

$$n_{\text{overall}} = (\underline{n_1} + \underline{n_2} + \underline{n_3})/3$$

The overall normal vector for the measurement point is taken as the average of that due to the various possible combinations of cross products between the vectors to the nearest neighbouring points. The normal-vectors have unit length.

The estimated position of the surface is calculated using the "surface normal vector" for the adjacent points (or the average of these, if there are more than two nearest neighbours). If the last measured point is specified by $r_n$, $\theta_n$ and $\Phi_n$, the position of the next point, given by $r_{n+1}$, $\theta_{n+1}$ and $\Phi_{n+1}$ (Φ is constant for each line-scan, by definition, although it increments at the end of each line-scan), is estimated by $$r_{n+1} = r_n + \Delta r$$

$$\theta_{n+1} = \theta_n + \Delta\theta = \theta_n + (\Delta L/r \sin \Phi_n)$$

The updated r coordinate $r_{n+1}$ is calculated as follows:

Let $\underline{n}$ be the unity-magnitude vector along the surface normal direction of the last measured point (or other nearest neighboring points) and $\underline{r_n}$ be the vector described by the coordinates $r_n$, $\theta_n$ and $\Phi_n$. We define a second vector $\underline{r'_n}$ with the same magnitude as $\underline{r_n}$ (i.e. $|r_n| = r'_n$), but new angular coordinates $\theta_{n+1}$ and $\Phi_{n+1}$. Often $\Phi_{n+1} = \Phi_n$, except at the end of each θ scan.

The estimated r coordinate of the n+1 point, $r_{n+1}$ is given by:

$$r_{n+1} = \underline{r_n}[(\underline{n} \cdot \underline{r_n})/(\underline{n} \cdot \underline{r'_n})] = \underline{r_n}[\cos \xi_n / \cos \xi_{n+1}]$$

where the dot indicates the scalar product of two vectors. $\xi_n$ represents the angle between $\underline{n}$ and $\underline{r_n}$ and $\xi_{n+1}$ represents the angle between $\underline{n}$ and $\underline{r_{n+1}}$.

The estimated surface normal vector for the n+1 point is then the average of the surface normals of one or more of its nearest neighbours.

Once the estimated position and estimated surface normal vector of the n+1 point has been calculated, the probe head is moved accordingly to bring the THz focus to this position and maintain the probe orientation along the surface normal of the new position. A THz waveform is then acquired at this new estimated position.

In areas of excessive deviation from the known position, the THz signal may be entirely absent (i.e. the THz reflection from very highly mis-oriented surfaces may not be reflected into the receiving optics at all). In these areas, where the THz signal is too small to provide a useful measure of the surface position, a best-guess of the surface geometry is made, based on interpolation/extrapolation from adjacent areas of more accurately determined surface geometry.

Therefore, in this way, the scan over the object surface is performed while simultaneously tracking the surface. In this regard, the THz waveforms provide a representation of the radiation reflected from the sample, both from the surface and internally, and provide an explicit measure of the deviation of the sample surface relative to the known surface position.

Referring again to FIG. 4, with the n positions on the object surface about the $\Phi_1$ trajectory determined, the area about the start point that is bounded these positions can be extrapolated and is therefore "known".

Once a line scan has been completed for $\Phi_1$, it is then incremented according to the same formula as in (1):

$$\Phi_2 = \Phi_1 + \Delta\Phi_1 = \Phi_1 + (\Delta L/r_1) \qquad (3)$$

A smaller value for $\Delta\Phi_1$ may be chosen to improve accuracy, in some cases.

From this new $\Phi_2$ position, a line-scan over the $\theta$ trajectory from 0 to $2\pi$ is performed. Referring to FIG. 4, the scan head moves in the same trajectory about the object, as represented by the dotted outline. The surface positions on the sample that are scanned about this new $\Phi_2$ position correspond to the second loop around the start point.

Again n surface positions about the $\Phi_2$ position are scanned, with n calculated as per equation (2), for each $\Phi$-value.

This procedure of incrementing $\Phi$ and scanning the object about a trajectory related to each $\Phi$ position enables the "known area" of the sample to expanded upon, as shown in FIG. 4, where each ring represents the positions scanned for different $\Phi$ positions. This is also represented in FIG. 8, where $\Phi_0$ is the start position, and the first trajectory about $\Phi_0$ is for $\Phi_1$, which has 6 positions on the object surface where a waveform is obtained. The next trajectory is for $\Phi_2$, which has 12 positions on the object surface where a waveform is obtained, and so on.

In this way $\Phi$ can be incremented across the entire $\Phi$ range (from 0 to $\pi$) in order to cover the entire surface area of the object. Alternatively, $\Phi$ can be incremented over an alternative predetermined scan-range, in order to cover only a particular surface area of the object.

This procedure can be used to measure both the surface geometry and the object surface layer structure/composition simultaneously. Once the scanning procedure is complete, the data has the form of a set of THz waveforms (each corresponding to a specific position on the object surface), with corresponding surface positions and surface normal vectors (which indicate the specific orientation of each surface position).

Where the object is a tablet, various parameters of the tablet coating may be extracted from the THz waveforms, such as the number of coating layers or the thickness of the coating layers. In this regard, the internal reflections can indicate material interfaces and also inhomogeneities within the sample.

These values may be plotted over a model of the tablet surface obtained from the measured tablet geometry. This is shown in FIG. 9, where a THz waveform is illustrated, and indicates the correspondence of the features in the waveform against a tablet cross-section.

Also, FIG. 10 illustrates a slice through a volume dataset obtained using the scanning measurements, such as shown in FIG. 9. This volume dataset is compared against the outline of a tablet, on the left, so as to show the different material interfaces that the present invention can extract from a closed surface object.

Further, FIG. 12 illustrates the three dimensional data set of FIG. 10 for the coating structure of a tablet 100 as a slice through its volume. This slice through the volume dataset is also illustrated in the Figure as an image of the cross section. The image has plotted the depth against lateral position, and clearly shows material interfaces of the tablet. That is, the image shows the thickness of an outer coating and also the thickness of an inner coating. By generating cross section images, like this, it is possible to control the quality of such tablets, such as by ensuring they have a consistent coating thickness.

The present invention may be implemented in an production environment. In this regard, with reference to FIG. 13, there are illustrated examples of the use of fiber-delivered THz probes. On the left of the figure, a production line example is shown which utilises multiple probes in fixed positions to image the tablet as it moves along the conveyor belt. This technique is therefore an "on-line" process, which obtains measurements from predetermined locations on multiple tablets in order to provide quality control. On the right of the figure, a single probe attached to a robot arm manipulator in an offline testing system is illustrated. The sample is fixed in a sample holder and, in this example, the robot arm moves the probe about six different axes in order to investigate and image the sample.

Alterations and additions are possible within the general inventive concepts. The embodiments of the invention are to be considered as illustrations of the invention and not necessarily limiting on the general inventive concepts.

For instance, the single scan technique using polar coordinates may be utilised as an iterative process. Once surface positions and surface normals for those positions have been determined, the scanning head can navigate about the phi position while maintaining a predetermined distance from the determined surface positions and perpendicular thereto and rescanning in the process. If the results of the re-scan indicate that the deviation between the actual surface geometry and the current estimate are below a predetermined level, then the surface geometry estimate can be considered acceptable and characteristics of the object surface/coating structure may be reliably obtained from the data. If however, significant differences between the previous geometry estimate and the results of the last scan are apparent (or there remains surface regions without reliable THz reflection data), then the scanning procedure will be repeated using the updated geometry estimate. This iterative scanning process can then be repeated until the geometry estimate is considered sufficiently accurate. In other words, a more refined estimation of the surface geometry may be obtained by performing a further scan over the sample surface such that the THz probe head tracks the surface geometry as per the result obtained previously.

The invention claimed is:

1. A method of investigating a non-planar sample comprising:
providing at least one emitter for irradiating the non-planar sample;
irradiating the sample with radiation having at least one frequency in the range from 25 GHz to 100 THz at a plurality of points on a non-planar surface of the sample, the plurality of points comprising a first point and a second point, wherein the first point is irradiated by modifying the relative orientation and positioning of the emitter and the sample and by irradiating the first point when the emitter and the sample are orientated and positioned such that the radiation is incident upon the sample at a predetermined angle of incidence to the surface of the sample at the first point and the emitter is positioned at a predetermined distance with respect to the first point, and the second point is irradiated by modifying the relative orientation and positioning of the emitter and the sample, and irradiating the second point when the emitter and the sample are orientated and positioned such that the radiation is incident upon the sample at the predetermined angle of incidence to the surface of the sample at the second point and the emitter is positioned at the predetermined distance with respect to the second point;

detecting radiation reflected from the sample, wherein said predetermined angle of incidence to the surface of the sample and said predetermined distance are selected to maximize the amplitude and/or bandwidth of the detected reflected radiation.

2. The method of claim 1 further comprising analyzing the detected radiation to determine characteristics of one or more surface layers of the sample.

3. The method of claim 2 wherein the characteristics determined relate to the thickness of one or more surface layers of the sample.

4. The method of claim 1 further comprising analyzing the detected radiation to determine a geometry of one or more surface layers of the sample.

5. The method of claim 1 further comprising generating an image of one or more surface layers of the sample using the detected radiation.

6. The method of claim 1 further comprising:

actuating the emitter and/or the sample to enable the emitter to move relative to the sample about a first trajectory from a first irradiated point such that the plurality of points lie on the first trajectory.

7. The method of claim 6 further comprising:

repositioning the emitter at an angle to the first trajectory, the angle lying on a second trajectory, such that the second trajectory is in a plane perpendicular to a plane of the first trajectory;

repeating the actuating and irradiating steps about a third trajectory parallel with the first trajectory; and detecting radiation transmitted and/or reflected from the sample at a second plurality of points about the third trajectory.

8. The method of claim 7 further comprising repeating the repositioning of the emitter along a range of angles along the second trajectory in order to obtain additional detection measurements.

9. The method of claim 6 further comprising forming an image representative of one or more surface layers of the sample using the detected radiation.

10. The method of claim 1 wherein the predetermined distance corresponds to a focal distance of the emitter.

11. The method of claim 1, further comprising characterizing one or more surface layers of a pharmaceutical sample.

12. The method of claim 11 wherein the one or more surface layers include a coating of the pharmaceutical sample.

13. Apparatus for investigating a sample having a non-planar surface, the apparatus comprising:

at least one emitter for irradiating the sample with radiation having at least one frequency in the range from 25 GHz to 100 THz at a plurality of points on a surface of the sample; and a detector for detecting radiation reflected from the sample, wherein the plurality of points comprises a first point and a second point and the apparatus is operable to irradiate the first point by modifying the relative orientation and positioning of the emitter and the sample and by irradiating the first point when the emitter and the sample are positioned such that the radiation is incident upon the sample at a predetermined angle of incidence to the surface of the sample at the first point and the emitter is positioned at a predetermined distance with respect to the first point, and the apparatus is operable to irradiate the second point by modifying the relative orientation and positioning of the emitter and the sample and by irradiating the second point when the emitter and the sample are positioned such that the radiation is incident upon the sample at the predetermined orientation angle of incidence to the surface of the sample at the second point and the emitter is positioned at the predetermined distance with respect to the second point, wherein said predetermined angle of incidence to the surface of the sample and said predetermined distance are selected to maximize the amplitude and/or bandwidth of the detected reflected radiation.

14. Apparatus of claim 13 further comprising means for actuating the emitter and/or the sample to enable the emitter to move relative to the sample about a first trajectory from a first irradiated point such that the plurality of points lie on the first trajectory.

15. Apparatus of claim 14 wherein the means for actuating comprises a robot arm.

16. Apparatus of claim 15 wherein the robot arm is at least a five-axis motion system.

17. Apparatus of claim 13 wherein the emitter is housed in a fiber-coupled probe head.

18. Apparatus according to claim 13, comprising a plurality of fixed emitters, each provided at said predetermined angle of incidence and said predetermined distance with respect to a different point of the plurality of points on the non-planar surface of said sample.

19. The method of claim 1, further comprising determining whether the emitter is the predetermined distance from one point of the plurality of points by comparing the radiation reflected from the sample with a reference waveform.

20. The method of claim 1, further comprising finding the predetermined angle of incidence to the surface of the sample for a point of the plurality of points by varying the orientation of the emitter relative to the sample and determining the predetermined angle of incidence as the angle of incidence in which the amplitude and/or bandwidth of the reflected radiation is a maximum.

21. The method of claim 1, further comprising determining an estimate of the predetermined distance and the predetermined angle of incidence for a first point of the plurality of points and maintaining the estimated distance and angle of incidence for a second point of the plurality of points.

* * * * *

UNITED STATES PATENT AND TRADEMARK OFFICE
CERTIFICATE OF CORRECTION

PATENT NO. : 8,665,423 B2
APPLICATION NO. : 10/569374
DATED : March 4, 2014
INVENTOR(S) : Withers et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 849 days.

Signed and Sealed this

Twenty-ninth Day of September, 2015

Michelle K. Lee
*Director of the United States Patent and Trademark Office*